United States Patent [19]

Nasser

[11] Patent Number: 4,866,977
[45] Date of Patent: Sep. 19, 1989

[54] MINI AIR METER FOR FRESH CONCRETE

[76] Inventor: Karim W. Nasser, University of Saskatchewan, Dept. of Civil Eng., Saskatoon, SK S7N OWO, Canada

[21] Appl. No.: 281,452

[22] Filed: Dec. 8, 1988

[51] Int. Cl.$^4$ .............................................. G01N 7/16
[52] U.S. Cl. ....................................... 73/19; 73/61 R
[58] Field of Search ................................... 73/19, 61 R

[56] References Cited

U.S. PATENT DOCUMENTS

| | | | |
|---|---|---|---|
| 2,635,459 | 4/1953 | Gray | 73/19 |
| 2,668,437 | 2/1954 | Patch | 73/19 |
| 2,722,825 | 11/1955 | Meyer | 73/19 |
| 2,823,540 | 2/1958 | Patch | 73/19 |
| 2,892,343 | 6/1959 | Chace | 73/19 |
| 4,344,316 | 8/1982 | Nasser | 73/19 |

Primary Examiner—Stewart J. Levy
Assistant Examiner—Joseph W. Roskos
Attorney, Agent, or Firm—Irell & Manella

[57] ABSTRACT

A volumetric test apparatus for entrained air contents of regular and lightweight fresh concrete comprises an outer container, an inner bowl, an upper tapered top section detachably securable to the outer container and a cover and rod for the top section. The concrete sample is placed in the bowl and rodded with the rod to eliminate any large entrapped air voids. The bowl is then placed in the outer container which is then filled with water and the top section is sealably locked in place upon the outer container and is also filled with water whereupon a cap is screw threadably engaged upon the cover. After manual agitation, the cap is removed allowing previously entrained air to escape and the top and container is then topped up with alcohol which is measured as it is poured into the apparatus. The volume of the entrained air may then be calculated readily and easily.

16 Claims, 2 Drawing Sheets

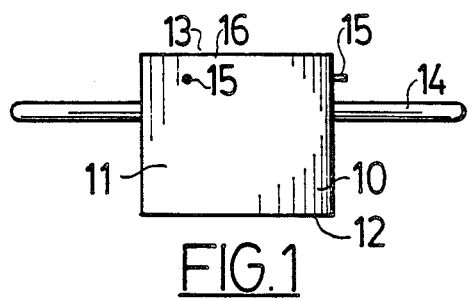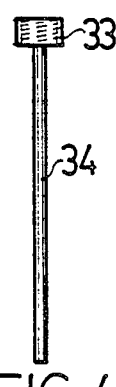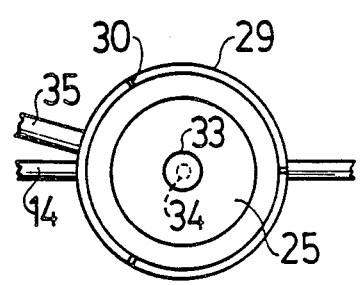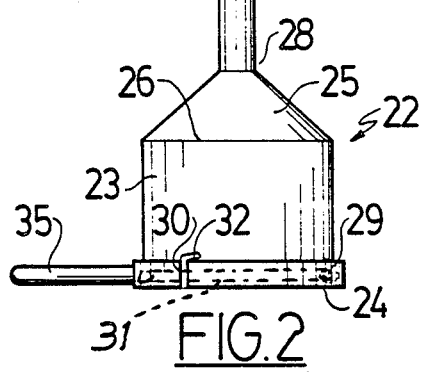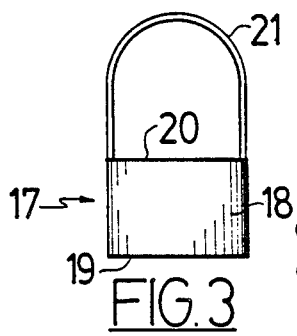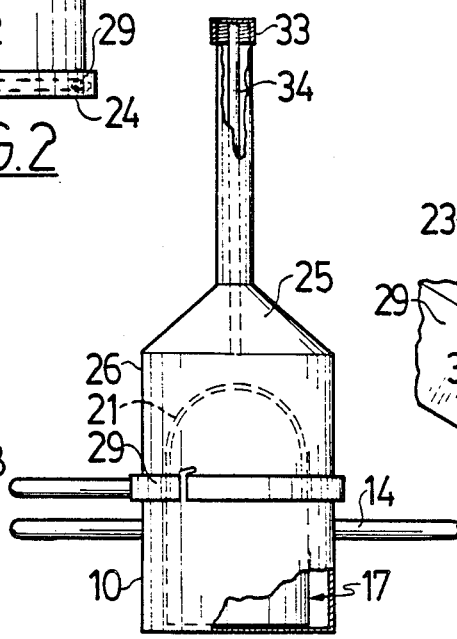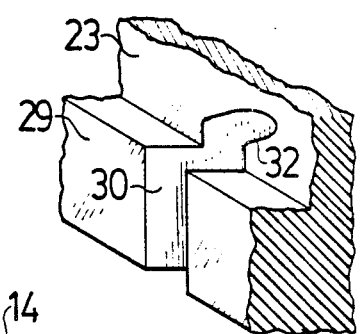

MINI AIR METER FOR FRESH CONCRETE

BACKGROUND OF THE INVENTION

This invention relates to new and useful improvements in apparatus used to determine the air content of fresh concrete and in particular to determine the air content of fresh concrete containing normal and lightweight aggregate.

It is well known that proper use of entrained air in concrete can produce significant improvements in important properties such as workability in fresh concrete and frost resistance in hardened concrete.

Conventionally, a number of test methods have been developed to determine this air content and four such methods are in current use. These include pressure tests, gravimetric tests, volumetric tests for fresh concrete and microscopic linear traverse or point count methods for hardened concrete.

It has been found that only the volumetric method is suitable for use with both lightweight and normal density fresh concretes and is also suitable as a controlled test in the field.

However the major drawback of the present volumetric method is the relatively large sample size required, namely, 0.075 ft.$^3$ (2.1 liters).

When this weight of concrete sample is combined with that of the apparatus, it requires considerable physical effort to carry out the mixing which is so necessary to perform the test.

Other prior art known to applicant is listed below:

PRIOR ART

U.S. Pat. No. 2,635,459, Chesleigh Gray, issued Apr. 21, 1953. This comprises a cylindrical container with a conical cover securable to the container with the cover having various ports therein one of which permits pressurization of the interior. The device also is designed to measure the percentage of surface moisture on saturated discrete material.

U.S. Pat. No. 2,668,437, O. G. Patch, issued Feb. 9, 1954. This also is a pressure type apparatus as is the previous patent and of course requires a source of air and pressure.

U.S. Pat. No. 2,722,825, E. V. Meyer, issued Nov. 8, 1955. In this patent, the concrete is placed in the main container and includes a scale in which the zero point is situated near the top of a rod. The height of the sample now has to be determined by sighting along the top edge of the container and reading the scale on the rod. It will be noted that the container is not filled with concrete hence the requirement for this measurement.

U.S. Pat. No. 2,892,343, L. M. Chace, issued June 30, 1959. This is a volumetric apparatus utilizing a barrel and cup with a stopper at one end.

U.S. Pat. No. 4,344,316, K. W. Nasser (present applicant), issued Aug. 17, 1982. This discloses a chamber having an open end and an opposite closable end and provided with a heating device and pressure measuring device.

Publication: Mini Air Meter For Fresh Concrete by K. W. Nasser and B. D. Whaley, Concrete International, March, 1988 pp. 43–46.

The present invention overcomes disadvantages inherent with the prior art and present methods and in accordance with the invention there is provided apparatus for volumetrically determining the air content of fresh regular or lightweight concrete comprising in combination a base container, a concrete sample holding bowl detachably engageable within said container, with the upper side of said bowl being situated below the upper side of said base container, a cover component, said cover component including a hollow lower body portion selectively engageable in sealed relationship upon said base container, a hollow conical upper portion extending upwardly from said lower body portion and a vertically situated conduit extending upwardly from the apex of said conical upper portion and communicating with the interior thereof and a cap detachably and sealably engageable upon the upper end of said conduit.

Another aspect of the invention discloses a method of determining the entrained air content of fresh regular or lightweight concrete utilizing the apparatus according to claim 1, which comprises the steps of:

a. filling said concrete sample holding bowl with fresh concrete substantially flush with the upper side edge thereof;

b. rodding said concrete to eliminate substantially, relatively large entrapped air voids therein;

c. placing said bowl within said base container and filling said base container with water and flooding the upper surface of the concrete within said bowl;

d. sealably locking said cover component onto said base container;

e. filling said cover component with water up to the top of said conduit, and sealably engaging said cap upon the upper end of said conduit;

f. thoroughly agitating said apparatus to release substantially all entrained air in said fresh concrete sample;

g. placing said apparatus upright upon a supporting surface and removing said cap to release said entrained air;

h. topping up the water within said apparatus with an anti-foaming liquid to replace the released entrained air and measuring said liquid; and i. calculating the amount of escaped entrained air in said concrete sample from the amount of liquid added.

Another advantage of the present device is to provide a relatively simple apparatus based on the volumetric method to determine the air content of fresh concrete both regular and lightweight concrete. The results show that this device is reliable, easy to operate and portable enough for both field and laboratory use.

A still further advantage of the present invention is to provide a device and method of the character herewithin described which is simple in construction, economical in manufacture and otherwise well suited to the purpose of which it is designed.

With the foregoing in view, and other advantages as will become apparent to those skilled in the art to which this invention relates as this specification proceeds, the invention is herein described by reference to the accompanying drawings forming a part hereof, which includes a description of the best mode known to the applicant and of the preferred typical embodiment of the principles of the present invention, in which:

DESCRIPTION OF THE DRAWINGS

FIG. 1 is a side elevation of the base container per se;

FIG. 2 is a side elevation of the cover component per se;

FIG. 3 is a side elevation of the concrete sample holding bowl per se;

FIG. 4 is a side elevation of the cap assembly per se;

FIG. 5 is a side elevation of the assembled apparatus broken away in part to show the interior thereof;

FIG. 6 is a top plan view of FIG. 5;

FIG. 8 is a fragmentary isometric view of a portion of the cover and flange.

In the drawing like characters of reference indicate corresponding parts in the different figures.

DETAILED DESCRIPTION

Figure 7:
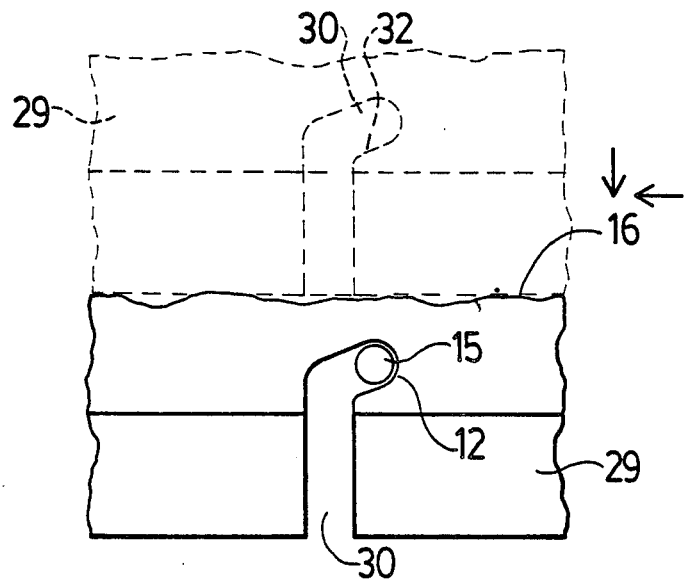
FIG. 7 is an enlarged fragmentary side elevation showing the preferred locking mechanism of the cover component to the base container.

Before proceeding with a description of the present invention, reference should be made to an article in Concrete International dated March, 1988 and entitled "Mini Air Meter For Fresh Concrete" by the applicant an another which is hereby incorporated by reference into the present application.

In this article it is mentioned that the current ASTM specification outlines four methods of determining air content of concrete, namely the pressure method, the gravimetric method, the volumetric method and microscopic linear traverse or point count method, the latter being for hardened concrete.

Current Canadian Standards Association specifications include pressure, volumetric and microscopic methods only.

As mentioned in the article, only the volumetric method is suitable for lightweight and normal density fresh concretes while also being suitable as a control test in the field and it will be noted that the major drawback of the current ASTM C173 volumetric method is the relatively large sample size, namely, 0.075 ft.$^3$ or 2.1 liters that is required to undertake the tests.

When this weight of concrete sample is combined with that of the apparatus, considerable physical effort is required to carry out the mixing which is necessary to perform the test.

The present apparatus overcomes this disadvantage although it is based on the same principals as the ASTM and CSA volumetric tests.

One of the principal differences, apart from the size of sample required and the relatively low weight apparatus, is the fact that a separate concrete sample holding bowl is utilized within the base component thus reducing clean out requirements to a minimum and eliminating many problems associated with sealing the cover component to the base component after one test has been completed and another is required.

Proceeding therefore to describe the invention in detail, reference should be made to the accompanying drawings in which 10 illustrates a cylindrical base container having a surrounding wall a base 12 and an open upper side 13.

A pair of handles 14 extend one upon each side of the wall 11 diametrically opposite one another and a plurality of locking pins 15 extend radially from the surrounding wall just below the upper edge 16 of the container and preferably spaced equidistantly therearound, the purpose of which will hereinafter be described.

A concrete sample holding bowl is provided collectively designated 17 and is also cylindrical in configuration including a surrounding wall 18, a base 19 and an open upper side 20 with a handle 21 overspanning this open upper side for facilitating placement and removal thereof into and out of the base container 10 and it will be noted that the height of the bowl 18 is slightly less than the height of the base container 10 into which it may be engaged.

FIG. 2 shows a cover component collectively designated 22 which includes a cylindrical lower body portion 23 having an open base 24 and a conical upper portion 25 extending from the upper side 26 of the surrounding wall 23, it being understood of course that both the lower body portion and the conical upper portion are hollow.

A conduit 27 extends upwardly from the apex 28 of the conical portion and terminates in an externally screw threaded upper end 28 and this conduit communicates with the interior of the conical portion 25 and of course the lower body portion 23.

Means are provided to detachably and sealably connect this cover component 22 upon the upper side of the base container 10 and in this connection it will be noted that a radially extending flange 29 is situated adjacent the lower open end 24 and extends radially therefrom. This flange is provided with a plurality of slots 30 there through, one for each pin 15 on the base container so that when the cover component is engaged upon the base container, it may be positioned so that the pins move upwardly through these slots to the surface of the part of the slot extension in the vertical wall of the lower body portion adjacent the flange 29 as shown in FIG. 7. An O-ring or other seal 31 shown in phantom in FIG. 2 is provided seated within the periphery of the flange and which is engaged by the upper edge 16 of the base container. Once the pins have passed through slots 30, the cover may be rotated clockwise so that the pins ride up small ramps 32 in the slots 30 and force the cover component into sealing engagement with the base container. Partial rotation of the cover component in an anti-clockwise direction will of course release the container by aligning the pins 15 with the portions of the slots in the flange 29 so that the cover component may be removed.

FIG. 4 shows a cylindrical cap 33 internally screw threaded and adapted to screw threadably engage the upper end 28 of the conduit 27 and a rod 34 is secured to the centre of the underside of this cap and extends downwardly into the conduit once the cap is screw threadably engaged upon the upper end 28 thereof.

It will also be noted that an operating handle 35 extends outwardly from one side of the flange 29 once again facilitating operation of the engagement and disengagement of the cover component with the base container as well as providing hand holds for manipulating the apparatus as will hereinafter be described.

The method of operation is as follows:

Firstly, fresh concrete is placed into the concrete sample holding bowl 17 in two substantially equal layers. Each layer is rodded approximately ten times with the rod 34 extending from the cap 33 and the sides of the bowl may be tapped approximately ten to fifteen times to remove any large entrapped air voids.

The surface of the concrete sample is struck off level with the bowl by a straight edge (not illustrated) whereupon the bowl 17 is placed within the base container 10 and because of the size of the bowl as hereinbefore described, the upper edge 20 will be situated below the upper edge 16 of the base container.

The base container may be filled approximately half full of water prior to the insertion of the bowl therein whereupon the water level should rise sufficiently to completely cover the concrete sample within the sample bowl 17. If necessary, more water is added until the sample is submerged.

The cover component 22 is then engaged with the upper side of the base container as hereinbefore described and rotated to sealably lock the two parts together.

Water is then added through the open neck of the conduit 27 until the apparatus is completely full whereupon the cap and rod are engaged within the conduit with the cap screw threadably engaging the upper end 28 thereof.

Utilizing measurements approximately similar to those indicated in the accompanying article, the total volume of the water in the apparatus is approximately 23 in.$^3$ (325 ml) which is approximately 1.7 times the volume of the concrete within the concrete sample holding bowl 17. These measurements and dimensions are exemplary only.

The water and concrete are mixed thoroughly by shaking and inverting the apparatus approximately ten times. Each time the apparatus is tipped, it is rotated about one quarter turn to assist in the mixing. After shaking, the cap 33 is unscrewed and removed and before taking the reading, a slender stiff wire (not illustrated) is preferably pushed down the conduit and into the tapered section 25 in order to ensure that no air is trapped in the cover section.

The reading is taken by measuring the amount of alcohol it takes to refill the apparatus completely. Alcohol is used rather than water in order to remove any foam that may have accumulated during the agitation and mixing of the sample.

The volume of air in the concrete sample is determined by subtracting the volume of water displaced by the rod 34 (approximately 6 mml) from the volume of alcohol required to refill the apparatus. Since the volume of the inner bowl in this example is 200 ml, the actual air content in percent is found by dividing the residual volume of alcohol by two.

As will be seen from the above identified article, the test results illustrate the reproducibility of this apparatus and method and show that it is sufficiently reliable when compared to the standard pressure meter.

Once the amount of air has been ascertained, the cover component may be removed together with the bowl 17 and the concrete discharged therefrom whereupon washing is relatively easy as compared with washing and rinsing of existing apparatus.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. Apparatus for volumetrically determining the air content of fresh regular or lightweight concrete comprising in combination a base container, a concrete sample holding bowl detachably engageable within said container, with the upper side of said bowl being situated below the upper side of said base container, a cover component, said cover component including a hollow lower body portion selectively engageable in sealed relationship upon said base container, a hollow conical upper portion extending upwardly from said lower body portion and a vertically situated conduit extending upwardly from the apex of said conical upper portion and communicating with the interior thereof and a cap detachably and sealably engageable upon the upper end of said conduit.

2. The apparatus according to claim 1 which includes means to selectively sealably engage said cover component with said base component, said means including a plurality of pins extending radially outwardly from the wall of said base container adjacent the upper side edge thereof, a radially extending flange adjacent the lower side end of the wall of said lower body portion of said cover component, slots formed through said flange engageable with said pins, ramps on said flange operatively connected to said slots upon which said pins engage as said cover component is partially rotated after said slots have engaged said pins and sealing means cooperating between said cover and said base container.

3. The apparatus according to claim 2 which includes a rod extending downwardly from the interior of said cap for rodding said concrete sample after it is placed within said concrete sample holding bowl, to eliminate substantially, any relatively large entrapped air voids in said concrete sample.

4. The apparatus according to claim 3 which includes means to sealably engage said cap with the upper end of said, conduit, said last mentioned means including said cap being internally screw threaded and being operatively engageable with the upper end of said conduit, said upper end of said conduit also being screw threaded, and operating handles extending from said base container and said cover component, the volume of said concrete sample holding bowl being approximately 200 milliliters.

5. A method of determining the entrained air content of fresh regular or lightweight concrete utilizing the apparatus according to claim 4, which comprises the steps of:
   a. filling said concrete sample holding bowl with fresh concrete substantially flush with the upper side edge thereof;
   b. rodding said concrete to eliminate substantially, relatively large entrapped air voids therein;
   c. placing said bowl within said base container and filling said base container with water and flooding the upper surface of the concrete within said bowl;
   d. sealably locking said cover component onto said base container;
   e. filling said cover component with water up to the top of said conduit, and sealably engaging said cap upon the upper end of said conduit;
   f. thoroughly agitating said apparatus to release substantially all entrained air in said fresh concrete sample;
   g. placing said apparatus upright upon a supporting surface and removing said cap to release said entrained air;
   h. topping up the water within said apparatus with an anti-foaming liquid to replace the released entrained air and measuring said liquid; and
   i. calculating the amount of escaped entrained air in said concrete sample from the amount of liquid added.

6. A method of determining the entrained air content of fresh regular or lightweight concrete utilizing the apparatus according to claim 3, which comprises the steps of:
   a. filling said concrete sample holding bowl with fresh concrete substantially flush with the upper side edge thereof;

b. rodding said concrete to eliminate substantially, relatively large entrapped air voids therein;
c. placing said bowl within said base container and filling said base container with water and flooding the upper surface of the concrete within said
d. sealably locking said cover component onto said base container;
e. filling said cover component with water up to the top of said conduit, and sealably engaging said cap upon the upper end of said conduit;
f. thoroughly agitating said apparatus to release substantially all entrained air in said fresh concrete sample;
g. placing said apparatus upright upon a supporting surface and removing said cap to release said entrained air;
h. topping up the water within said apparatus with an anti-foaming liquid to replace the released entrained air and measuring said liquid; and
i. calculating the amount of escaped entrained air in said concrete sample from the amount of liquid added.

7. The apparatus according to claim 2 which includes means to sealably engage said cap with the upper end of said conduit, said last mentioned means including said cap being internally screw threaded and being operatively engageable with the upper end of said conduit, said upper end of said conduit also being screw threaded, and operating handles extending from said base container and said cover component, the volume of said concrete sample holding bowl being approximately 200 milliliters.

8. A method of determining the entrained air content of fresh regular or lightweight concrete utilizing the apparatus according to claim 7, which comprises the steps of:
   a. filling said concrete sample holding bowl with fresh concrete substantially flush with the upper side edge thereof;
   b. rodding said concrete to eliminate substantially, relatively large entrapped air voids therein;
   c. placing said bowl within said base container and filling said base container with water and flooding the upper surface of the concrete within said
   d. sealably locking said cover component onto said base container;
   e. filling said cover component with water up to the top of said conduit, and sealably engaging said cap upon the upper end of said conduit;
   f. thoroughly agitating said apparatus to release substantially all entrained air in said fresh concrete sample;
   g. placing said apparatus upright upon a supporting surface and removing said cap to release said entrained air;
   h. topping up the water within said apparatus with an anti-foaming liquid to replace the released entrained air and measuring said liquid; and
   i. calculating the amount of escaped entrained air in said concrete sample from the amount of liquid added.

9. A method of determining the entrained air content of fresh regular or lightweight concrete utilizing the apparatus according to claim 2, which comprises the steps of:
   a. filling said concrete sample holding bowl with fresh concrete substantially flush with the upper side edge thereof;
   b. rodding said concrete to eliminate substantially, relatively large entrapped air voids therein;
   c. placing said bowl within said base container and filling said base container with water and flooding the upper surface of the concrete within said bowl;
   d. sealably locking said cover component onto said base container;
   e. filling said cover component with water up to the top of said conduit, and sealably engaging said cap upon the upper end of said conduit;
   f. thoroughly agitating said apparatus to release substantially all entrained air in said fresh concrete sample;
   g. placing said apparatus upright upon a supporting surface and removing said cap to release said entrained air;
   h. topping up the water within said apparatus with an anti-foaming liquid to replace the released entrained air and measuring said liquid; and
   i. calculating the amount of escaped entrained air in said concrete sample from the amount of liquid added.

10. The apparatus according to claim 1 which includes a rod extending downwardly from the interior of said cap for rodding said concrete sample after it is placed within said concrete sample holding bowl, to eliminate substantially, any relatively large entrapped air voids in said concrete sample.

11. The apparatus according to claim 10 which includes means to sealably engage said cap with the upper end of said conduit, said last mentioned means including said cap being internally screw threaded and being operatively engageable with the upper end of said conduit, said upper end of said conduit also being screw threaded, and operating handles extending from said base container and said cover component, the volume of said concrete sample holding bowl being approximately 200 milliliters.

12. A method of determining the entrained air content of fresh regular or lightweight concrete utilizing the apparatus according to claim 11, which comprises the steps of:
   a. filling said concrete sample holding bowl with fresh concrete substantially flush with the upper side edge thereof;
   b. rodding said concrete to eliminate substantially, relatively large entrapped air voids therein;
   c. placing said bowl within said base container and filling said base container with water and flooding the upper surface of the concrete within said bowl;
   d. sealably locking said cover component onto said base container;
   e. filling said cover component with water up to the top of said conduit, and sealably engaging said cap upon the upper end of said conduit;
   f. thoroughly agitating said apparatus to release substantially all entrained air in said fresh concrete sample;
   g. placing said apparatus upright upon a supporting surface and removing said cap to release said entrained air;
   h. topping up the water within said apparatus with an anti-foaming liquid to replace the released entrained air and measuring said liquid; and
   i. calculating the amount of escaped entrained air in said concrete sample from the amount of liquid added.

13. A method of determining the entrained air content of fresh regular or lightweight concrete utilizing the apparatus according to claim 10, which comprises the steps of:
   a. filling said concrete sample holding bowl with fresh concrete substantially flush with the upper side edge thereof;
   b. rodding said concrete to eliminate substantially, relatively large entrapped air voids therein;
   c. placing said bowl within said base container and filling said base container with water and flooding the upper surface of the concrete within said bowl;
   d. sealably locking said cover component onto said base container;
   e. filling said cover component with water up to the top of said conduit, and sealably engaging said cap upon the upper end of said conduit;
   f. thoroughly agitating said apparatus to release substantially all entrained air in said fresh concrete sample;
   g. placing said apparatus upright upon a supporting surface and removing said cap to release said entrained air;
   h. topping up the water within said apparatus with an anti-foaming liquid to replace the released entrained air and measuring said liquid; and
   i. calculating the amount of escaped entrained air in said concrete sample from the amount of liquid added.

14. The apparatus according to claim 1 which includes means to sealably engage said cap with the upper end of said conduit, said last mentioned means including said cap being internally screw threaded and being operatively engageable with the upper end of said conduit, said upper end of said conduit also being screw threaded, and operating handles extending from said base container and said cover component, the volume of said concrete sample holding bowl being approximately 200 milliliters.

15. A method of determining the entrained air content of fresh regular or lightweight concrete utilizing the apparatus according to claim 14, which comprises the steps of:
   a. filling said concrete sample holding bowl with fresh concrete substantially flush with the upper side edge thereof;
   b. rodding said concrete to eliminate substantially, relatively large entrapped air voids therein;
   c. placing said bowl within said base container and filling said base container with water and flooding the upper surface of the concrete within said bowl;
   d. sealably locking said cover component onto said base container;
   e. filling said cover component with water up to the top of said conduit, and sealably engaging said cap upon the upper end of said conduit;
   f. thoroughly agitating said apparatus to release substantially all entrained air in said fresh concrete sample;
   g. placing said apparatus upright upon a supporting surface and removing said cap to release said entrained air;
   h. topping up the water within said apparatus with an anti-foaming liquid to replace the released entrained air and measuring said liquid; and
   i. calculating the amount of escaped entrained air in said concrete sample from the amount of liquid added.

16. A method of determining the entrained air content of fresh regular or lightweight concrete utilizing the apparatus according to claim 1, which comprises the steps of:
   a. filling said concrete sample holding bowl with fresh concrete substantially flush with the upper side edge thereof;
   b. rodding said concrete to eliminate substantially, relatively large entrapped air voids therein;
   c. placing said bowl within said base container and filling said base container with water and flooding the upper surface of the concrete within said bowl;
   d. sealably locking said cover component onto said base container;
   e. filling said cover component with water up to the top of said conduit, and sealably engaging said cap upon the upper end of said conduit;
   f. thoroughly agitating said apparatus to release substantially all entrained air in said fresh concrete sample;
   g. placing said apparatus upright upon a supporting surface and removing said cap to release said entrained air;
   h. topping up the water within said apparatus with an anti-foaming liquid to replace the released entrained air and measuring said liquid; and
   i. calculating the amount of escaped entrained air in said concrete sample from the amount of liquid added.

* * * * *